US012016964B2

(12) United States Patent
Dang et al.

(10) Patent No.: US 12,016,964 B2
(45) Date of Patent: Jun. 25, 2024

(54) SYSTEM AND METHOD FOR AUTOMATING VERIFICATION OF MEDICAL INSTRUMENT STERILIZATION COMPATIBILITY AND STERILIZATION CYCLE SELECTION

(71) Applicant: ASP GLOBAL MANUFACTURING GMBH, Schaffhausen (CH)

(72) Inventors: Philipe K. Dang, San Diego, CA (US); Venkata Danam, Irvine, CA (US); Jeremy M. Yarwood, Aliso Viejo, CA (US); Yaeer Lev, Redondo Beach, CA (US); Brian J. Thompson, Aliso Viejo, CA (US); Amy K. Smith, Yorba Linda, CA (US); Sora Rhee, Pennsylvania Furnace, PA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 463 days.

(21) Appl. No.: 17/225,394

(22) Filed: Apr. 8, 2021

(65) Prior Publication Data
US 2021/0220503 A1 Jul. 22, 2021

Related U.S. Application Data

(62) Division of application No. 16/021,207, filed on Jun. 28, 2018, now Pat. No. 11,000,614.

(51) Int. Cl.
*A61L 2/24* (2006.01)
*A61L 2/07* (2006.01)
(Continued)

(52) U.S. Cl.
CPC .................. *A61L 2/24* (2013.01); *A61L 2/07* (2013.01); *A61L 2/14* (2013.01); *A61L 2/26* (2013.01);
(Continued)

(58) Field of Classification Search
CPC ..................................... A61L 2/24; A61L 2/07
See application file for complete search history.

(56) References Cited

U.S. PATENT DOCUMENTS 6,485,978 B1 * 11/2002 Kirckof ................. G09F 3/0297
436/1
2019/0290796 A1 * 9/2019 Ma ......................... G16H 40/20

OTHER PUBLICATIONS

Communication pursuant to Article 94(3) EPC dated Mar. 16, 2022 in a corresponding European patent application No. EP19762839.9.†

(Continued)

*Primary Examiner* — Kevin Joyner
(74) *Attorney, Agent, or Firm* — Lerner David LLP

(57) ABSTRACT

A sterilization system includes a communication hub that is configured to transfer information between devices of the system such as a sterilizing cabinet, biological indicator analyzer, and a server in order to allow a user to track a medical device throughout a sterilization process. The server may provide data to the sterilizing cabinet during a sterilization process that may be used to verify that the medical device is compatible with the sterilizing cabinet, and to automatically select a compatible sterilization cycle to perform on the medical device. Automatic selection of sterilization cycles and confirmation of compatibility reduces the possibility for user error, which could result in contaminated medical devices being placed back into service. Automatic selection of sterilization cycles also allows users to more efficiently configure and perform sterilization cycles while being confident that the medical device will be sterile upon completion.

19 Claims, 14 Drawing Sheets

(51) Int. Cl.
*A61L 2/14* (2006.01)
*A61L 2/26* (2006.01)
*A61B 1/12* (2006.01)
*A61L 2/20* (2006.01)

(52) U.S. Cl.
CPC ............... *A61B 1/121* (2013.01); *A61L 2/206* (2013.01); *A61L 2/208* (2013.01); *A61L 2202/122* (2013.01); *A61L 2202/24* (2013.01)

(56) References Cited

OTHER PUBLICATIONS

Getinge T-DOC User's Guide and Reference, Getinge Lunatronic ApS, 1995-2003.†
T-DOC—Instrument Intelligence Take Command of Your Operations, Getinge IT Solutions ApS, Apr. 2006.†
Getinge T-DOC Brochure, https://issuu.com/getinge/docs/sal2157_03_us_-_getinge_t-doc_brochure, Feb. 7, 2008.†

\* cited by examiner
† cited by third party

FIG. 7

Cycle# 1677, STERRAD 03, CSSD — 512

Devices in Load: — 514

STERRAD® System validation status as of 08/30/2017

[Print Page]

Device Information

| | STERRAD® 100NX System with ALLClear™ Technology | STERRAD® 100NX System | STERRAD® NX System with ALLClear™ Technology | STERRAD® NX System | STERRAD® 100S System | STERRAD® 200 System | add/remove |
|---|---|---|---|---|---|---|---|
| DEVICE MANUFACTURER Acclarent, Inc. DEVICE NAME Cyclops Multi-Angle Endoscope (Adapters 1 and 2) MODEL NUMBER CYE002 | ✓ Standard | | ✓ Standard | | ✓ | | ⊗ remove from My Devices |
| DEVICE MANUFACTURER Acclarent, Inc. DEVICE NAME Storz Adapter MODEL NUMBER SISLGCASTORZ | ✓ Standard | | ✓ Standard | | ✓ | | ⊗ remove from My Devices |

516
518
520

Cycles Summary | IMS Summary | Cycles Files | Sterility Guide Assurance

Your Hospital
ID: 5300170091

| My Hospital Devices | Recently Viewed | My Support Resources | All Departments ▾ |

Hospital Instrumentation:

SORT BY: Most Recent ▾

——— STERRAD® System validation status as of 08/30/2017 ———

Print Page

| Device Information | STERRAD® 100NX System with ALLClear™ Technology / STERRAD® 100NX System | STERRAD® NX System with ALLClear™ Technology / STERRAD® NX System | STERRAD® 100S System | STERRAD® 200 System |
|---|---|---|---|---|
| DEVICE MANUFACTURER: Richard Wolf<br>DEVICE NAME: Flexible Video Cystoscope<br>YOUR NUMBER: 7308.0614<br>MANUFACTURER NOTATION: Must be processed in the Advanced Cycle using an EtO... more | ✓ FLEX<br>✓ DUO | ✓ Advanced | | remove |
| DEVICE MANUFACTURER: Medovations<br>DEVICE NAME: M-Flex® Silicone Bougie<br>MODEL NUMBER:<br>MANUFACTURER NOTATION: Tray weight limit of 4850 grams (10.7 lbs) per shelf. more | | ✓ Standard | ✓ | remove from My Devices |
| | | | | remove from My |

FIG. 12

SYSTEM AND METHOD FOR AUTOMATING VERIFICATION OF MEDICAL INSTRUMENT STERILIZATION COMPATIBILITY AND STERILIZATION CYCLE SELECTION

BACKGROUND

Re-usable medical devices such as certain surgical instruments, endoscopes, etc., may be sterilized before re-use to minimize the likelihood that a contaminated device might be used on a patient. Various sterilization techniques may be employed, such as steam, hydrogen peroxide, and vapor phase sterilization, either with or without a gas plasma and ethylene oxide (EtO).

Sterilization of medical devices may be performed with an automated sterilization system such as a STERRAD® System by Advanced Sterilization Products of Irvine, California. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; and U.S. Pat. No. 6,447,719, entitled "Power System for Sterilization Systems Employing Low Frequency Plasma," issued Sep. 10, 2002, the disclosure of which is incorporated by reference herein. Each different medical device may require a different arrangement and sterilization process.

While a variety of systems and methods have been made and used for medical device sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 7 depicts an exemplary interface for viewing compatibility information for a device in a sterilization cycle;

FIG. 8 depicts an exemplary interface for viewing compatibility information for multiple devices in a sterilization cycle;

FIG. 9 depicts an exemplary interface for viewing a historic record of sterilization cycles and medical device compatibility;

FIG. 12 depicts an exemplary interface for viewing compatibility information for all devices currently in use;

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Overview of Exemplary Sterilization System

Figure 1:
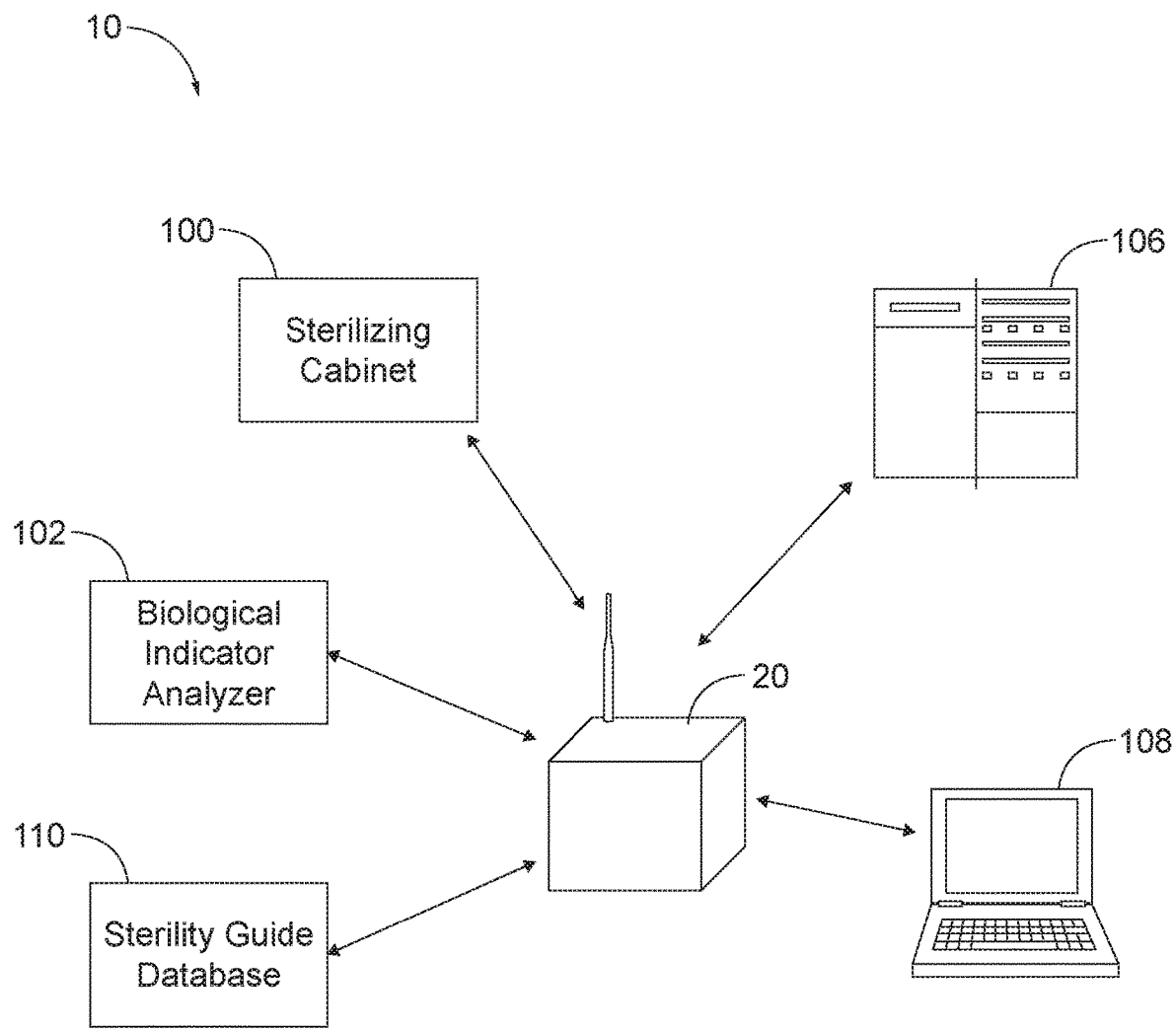
FIG. 1 depicts a schematic view of an exemplary sterilization system.

FIG. 1 depicts a schematic view of an exemplary system (10) of interconnected devices that may be configured to perform methods associated with sterilizing medical devices (e.g., endoscopes and other medical devices). System (10) of this example includes a sterilizing cabinet (100), a biological indicator analyzer (102), a communication hub (20), a server (106), a user device (108), and a sterility guide database (110). Communication hub (20) is configured to provide transmission of data between sterilizing cabinet (100), biological indicator analyzer (102), communication hub (20), server (106), user device (108), and sterility guide database (110), as will be described in greater detail below.

Figure 2:
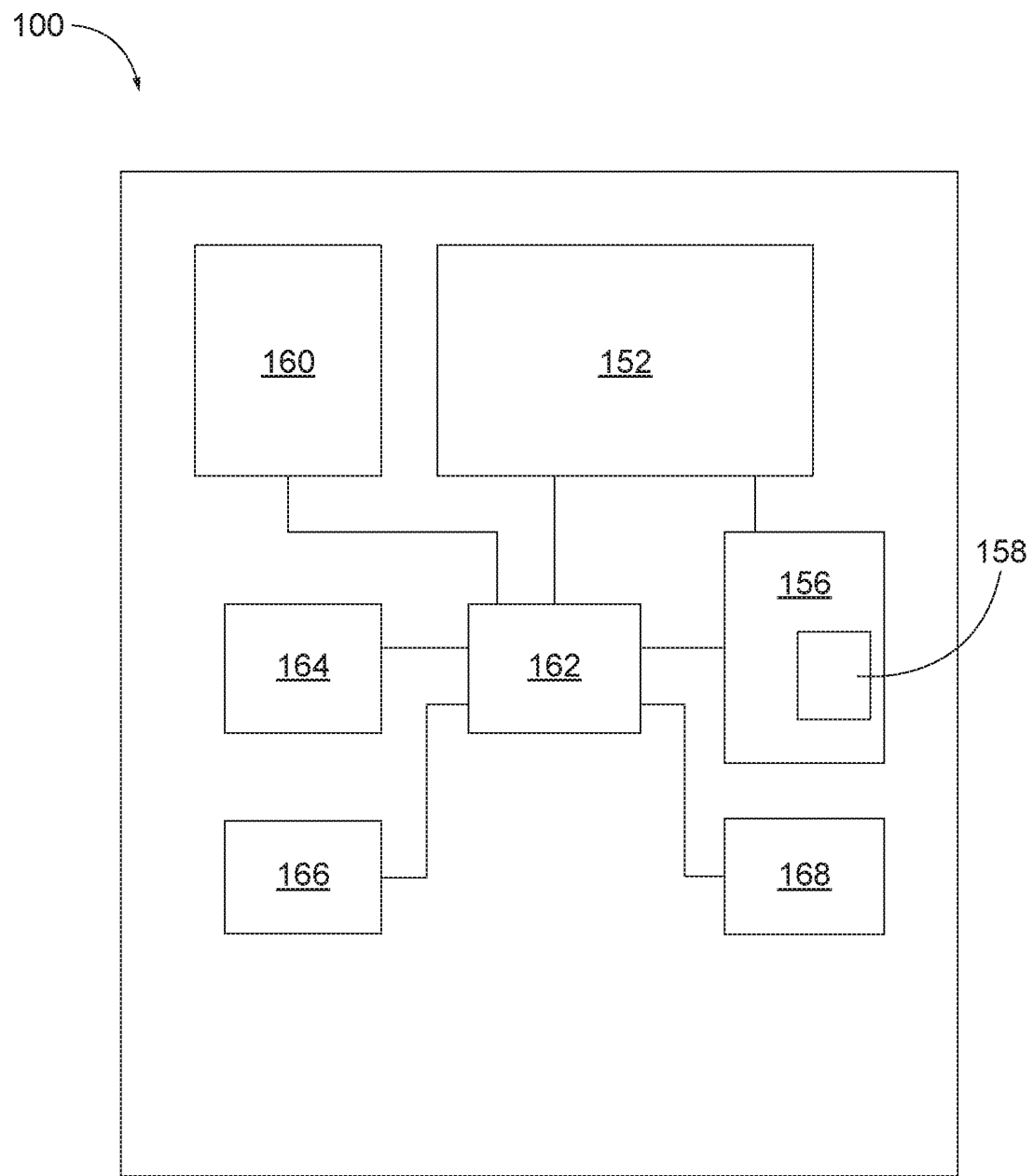
FIG. 2 depicts a schematic view of an exemplary sterilizing cabinet that may be used with the system of FIG. 1.

FIG. 2 depicts an exemplary set of components that may be incorporated into sterilizing cabinet (100). Sterilizing cabinet (100) may be configured to perform one or more sterilization cycles, with different sterilization cycles being appropriate for different types and quantities of medical devices. Sterilizing cabinet (100) of the present example includes a sterilization chamber (152), which is configured to receive one or more medical devices for sterilization. Sterilizing cabinet (100) also includes a sterilization module (156) that is operable to receive sterilant cartridges (158) and dispense a sterilant from a cartridge (158) into sterilization chamber (152). Sterilizing cabinet (100) further includes a touch screen display (160), which is operable to render various user interface display screens and receive user input in the form of the user contacting touch screen display (160). Sterilizing cabinet (100) may include various other kinds of user input features, including but not limited to buttons, keypads, keyboards, a mouse, a trackball, etc.

Sterilizing cabinet (100) of the present example further includes a processor (162), a communication module (164), a reader (166), and a memory (168). Processor (162) is in communication with the various components of sterilizing cabinet (100) and is operable to process data and execute control algorithms to drive various components of sterilizing cabinet (100). Communication module (164) is configured to enable bidirectional communication between sterilizing cabinet (100) and communication hub (20). Communication module (164) may also be configured to enable bidirectional communication between sterilizing cabinet (100) and server (106) and/or sterility guide database (110). Reader (166) is operable to read an identification tag of a biological indicator and/or other devices as described herein. Memory (168) is operable to store control logic and instructions and that are executed by processor (162) to drive components of sterilizing cabinet (100). Memory (168) may also be used to store results associated with setup of a sterilization cycle, performance of a load conditioning cycle, performance of a sterilization cycle, and/or various other kinds of information. Various suitable components and configurations that may be used to form processor (162), communication module (164), reader (166), and memory (168) will be apparent to those skilled in the art in view of the teachings herein.

In addition to the foregoing, sterilizing cabinet (100) may be configured and operable in accordance with at least some of the teachings of any of the patent references previously cited herein; U.S. Pub. No. 2017/0252473, entitled "Apparatus and Method for Sterilizing Medical Devices," published Sep. 7, 2017, the disclosure of which is incorporated by reference herein; and/or U.S. Pub. No. 2017/0252474, entitled "Method of Sterilizing Medical Devices, Analyzing Biological Indicators, and Linking Medical Device Sterilization," published Sep. 7, 2017, the disclosure of which is incorporated by reference herein.

In some cases, a biological indicator may be included in sterilizing cabinet (100, 150) along with the medical device during the sterilization process. The biological indicator may be activated before placement to cause a microorganism contained therein to multiply unless it is successfully sterilized during the procedure. After the sterilization process, the number of microorganisms present in the biological indicator may be determined by the biological indicator analyzer (102) to ensure that the sterilization process was successful for the biological indicator, which will also indicate that the sterilization procedure was successful for the medical device. Biological indicator analyzer (102) may receive a biological indicator and measure one or more characteristics of the biological indicator to gather data that may be used to determine whether the biological indicator tests positive, indicating that contamination is present after a sterilization procedure; or negative, indicating that no contamination is present after the sterilization procedure.

By way of example only, the biological indicator and biological indicator analyzer (102) may be configured and operable in accordance with at least some of the teachings of U.S. Pub. No. 2017/0253845, entitled "Self-Contained Biological Indicator," published Sep. 7, 2017, the disclosure of which is incorporated by reference herein; U.S. Pub. No. 2017/0253905, entitled "Apparatus and Method for Analyzing Biological Indicators," published Sep. 7, 2017, the disclosure of which is incorporated by reference herein; U.S. Pub. No. 2017/0252474, entitled "Method of Sterilizing Medical Devices, Analyzing Biological Indicators, and Linking Medical Device Sterilization," published Sep. 7, 2017, the disclosure of which is incorporated by reference herein; and/or U.S. Pub. No. 2018/0071421, entitled "Biological Indicator with Variable Resistance," published Mar. 15, 2018, the disclosure of which is incorporated by reference herein.

Server (106) may comprise a hospital record server or hospital local area network server. Server (106) may receive information from sterilizing cabinet (100) relating to sterilization procedures performed by the sterilizing cabinet (100), such as sterilization procedure durations and results; whether a particular sterilization procedure provided a subsequent indication of biological contamination; the identification of a user or technician who initiated, canceled, or complete a sterilization procedure; consumable materials or supplies used during a sterilization procedure; diagnostic information and systems errors; and/or other information. Server (106) may also receive data from biological indicator analyzer (102) via communication hub (20).

User device (108) may comprise a device such as a laptop computer, a desktop computer, a mobile device such as a smartphone, tablet, or other mobile computing device; or a proprietary device having similar capabilities, such capabilities including wired or wireless communication with devices such as communication hub (20), a processor and memory, a display, a user interface, and other capabilities. User device (108) may be used to access and view information associated with one or more components (100, 102, 110, 106) of system (10) via communication hub (20); and may also be used to create or modify configurations and settings of communication hub (20) and connected devices. A user of user device (108) may view information and configure devices via, for example, a desktop software application, a mobile device software application, a web browser, or another software interface that may allow user device (108) to exchange information with communication hub (20). While only one user device (108) is shown in FIG. 1 as being in communication with communication hub (20), several user devices (108) may be in communication with communication hub (20). Similarly, several sterilizing cabinets (100), several biological indicator analyzers (102), several servers (106), and several sterility guide databases (110) may be in communication with communication hub (20).

Figure 3:
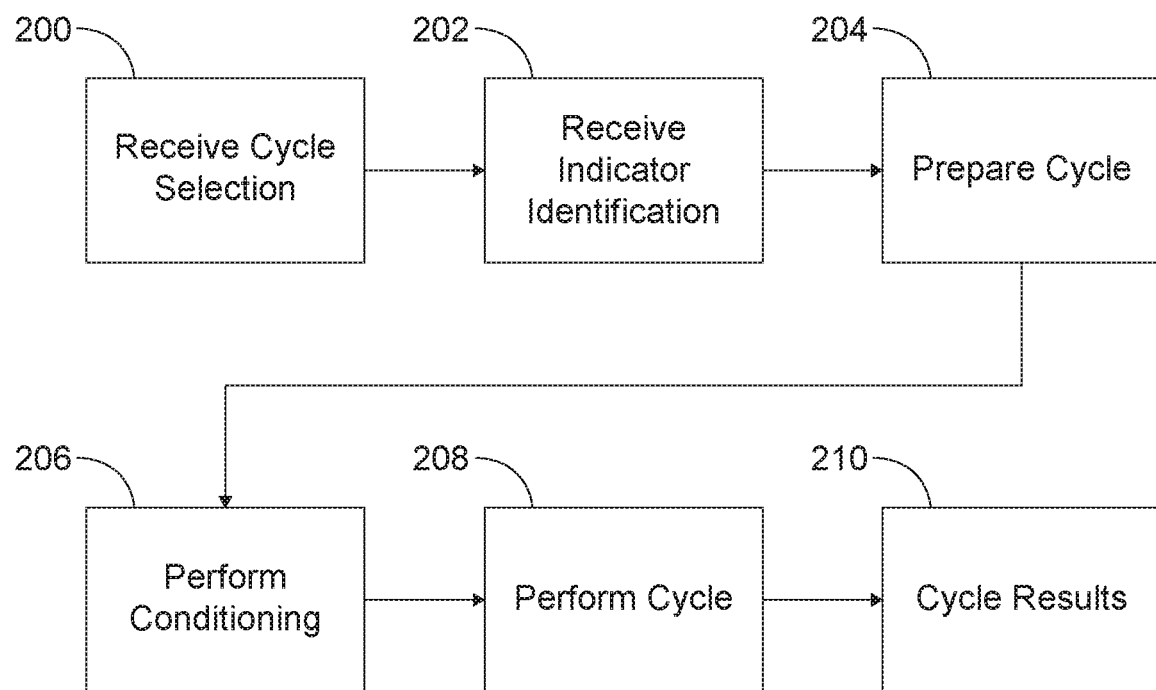
FIG. 3 depicts a high-level flowchart of an exemplary set of steps that a sterilizing cabinet of FIG. 2 could perform to sterilize a medical device.

Components (100, 102, 110, 106) of system (10) may each be coupled with communication hub (20) via any suitable wired and/or wireless communication technology, such as Ethernet, Wi-Fi, Bluetooth, USB, infrared, NFC, and/or other technologies. Communication hub (20) may relay data, etc., between components (100, 102, 110, 106) of system (10) as described herein, such that communication hub (20) serves as an intermediary. Various suitable components and configurations that may be used to form communication hub (20) will be apparent to those skilled in the art in view of the teachings herein. By way of example only, communication hub (20) and/or user device (108) may be configured and operable in accordance with at least some of the teachings of U.S. Pub. No. 2017/0252472, entitled "Apparatus and Method to Link Medical Device Sterilization Equipment," published Sep. 7, 2017, the disclosure of which is incorporated by reference herein; and/or U.S. Pub. No. 2017/0252474, entitled "Method of Sterilizing Medical Devices, Analyzing Biological Indicators, and Linking Medical Device Sterilization," published Sep. 7, 2017, the disclosure of which is incorporated by reference herein II. Overview of Exemplary Sterilization Process FIG. 3 depicts an exemplary set of steps that system (10) could perform to sterilize a medical device. Initially, sterilizing cabinet (100) may display one or more sterilization cycles via touch screen display (160) and then receive a sterilization cycle selection (block 200) from the user. Sterilizing cabinet (100) may also display instructions indicating whether a biological indicator should be used with the selected sterilization cycle; and receive a biological indicator identification (block 202). A biological indicator may be placed inside sterilization chamber (152) before the sterilization cycle begins and may remain in sterilization chamber (152) during a sterilization cycle. The user may thus identify the particular biological indicator (block 202) before the biological indicator is placed the sterilization chamber (152).

Selection of a sterilization cycle (block 200) and identification of a biological indicator (block 202) may define one or more requirements for the configuration and arrangement of medical devices within sterilizing cabinet (100). A door of sterilization chamber (152) may be opened and instructions may be displayed to guide a user through preparation of the sterilization cycle (block 204), including placement of the biological indicator, placement of medical devices, closing the door of sterilization chamber (152), and/or other changes in preparation. Before initiating the actual sterilization cycle (block 208), sterilization cabinet (100) may also perform load conditioning (block 206) of the medical devices that are loaded in sterilization chamber (152). Such load conditioning (block 206) may include verifying that sterilization chamber (152) is sealed; verifying contents of sterilization chamber (152); checking physical characteristics of the contents of sterilization chamber (152) such as moisture levels, content volume, content weight, internal temperature, or other characteristics; and/or performing one or more conditioning steps that may include heat treatment, chemical treatment, plasma treatment, or other types of treatment to reduce moisture, raise temperature, and/or otherwise prepare the medical devices in sterilization chamber (152) for the sterilization cycle.

Once the load conditioning (block 206) has been completed, the selected sterilization cycle itself may be performed (block 208). The sterilization cycle (block 208) may include exposing the medical device(s) in sterilizing chamber (152) to pressurized sterilant gas, further heat treatment, chemical treatment, plasma treatment, vacuum treatment, and/or other types of sterilization procedures. After the sterilization cycle (block 208) is completed, the complete sterilization results may be displayed to a user via touch screen display (160); transmitted to server (106); printed locally; and/or displayed, transmitted, and/or stored via other devices as may be desirable.

Sterilization cabinet (100) may also provide results (block 210) of the sterilization cycle. This provision of results (block 210) may include results from analysis of a biological indicator via biological indicator analyzer (102). These results may include a positive or negative indication of contamination present in the biological indicator at the completion of the sterilization cycle (block 208). In cases where the biological indicator suggests that contamination is present after completion of the sterilization cycle (block 208), additional actions may be taken such as alerting a user of the positive test and analysis of sterilization cycle history to determine if other past cycles may be the cause of the contamination; and/or if subsequently sterilized medical devices may need to be re-sterilized.

III. Exemplary Method for Identifying a Medical Instrument

Sterility guide database (110) comprises a set of records that associate a plurality of medical devices with a plurality of sterilization devices (e.g., sterilizing cabinet (100), etc.), sterilization procedures, sterilization cycles, and sterilization materials (e.g., biological indicators, detergents, sterilant, etc.); and indicate for each medical device association whether the particular sterilization device, procedure, or material has been verified as compatible or usable to sterilize that particular medical device. Sterility guide database (110) may comprise a database, table, file, or other data storage type stored on a computer (e.g., a cloud computer or cloud storage, server (106), or another physical server) and accessible to communication hub (20). Other locations and forms that sterility guide database (110) may take will be apparent to those skilled in the art in view of the teachings herein.

The exemplary methods described below may be implemented on a system such as system (10) to further mitigate the risk of human errors or equipment errors resulting in failed sterilization of medical devices, damage to medical devices, or waste of sterilization materials and resources. Several of the disclosed methods may benefit from identification of medical devices when the sterilization process is first configured to, for example, automatically select appropriate hardware and process configurations, verify compatibility, and take other similar steps based upon such an identification. Where the description or claims indicate that a step, determination, identification, or other decision or conclusion is performed "based on" or "based upon" certain input, data, or other factors, other factors or inputs may also influence the outcome. Accordingly, such descriptions should be interpreted to cover situations where the outcome is based only on or upon the described factors, as well as situations where the outcome is based at least on or upon the described factors in addition to others that are not explicitly described or listed.

Figure 4:
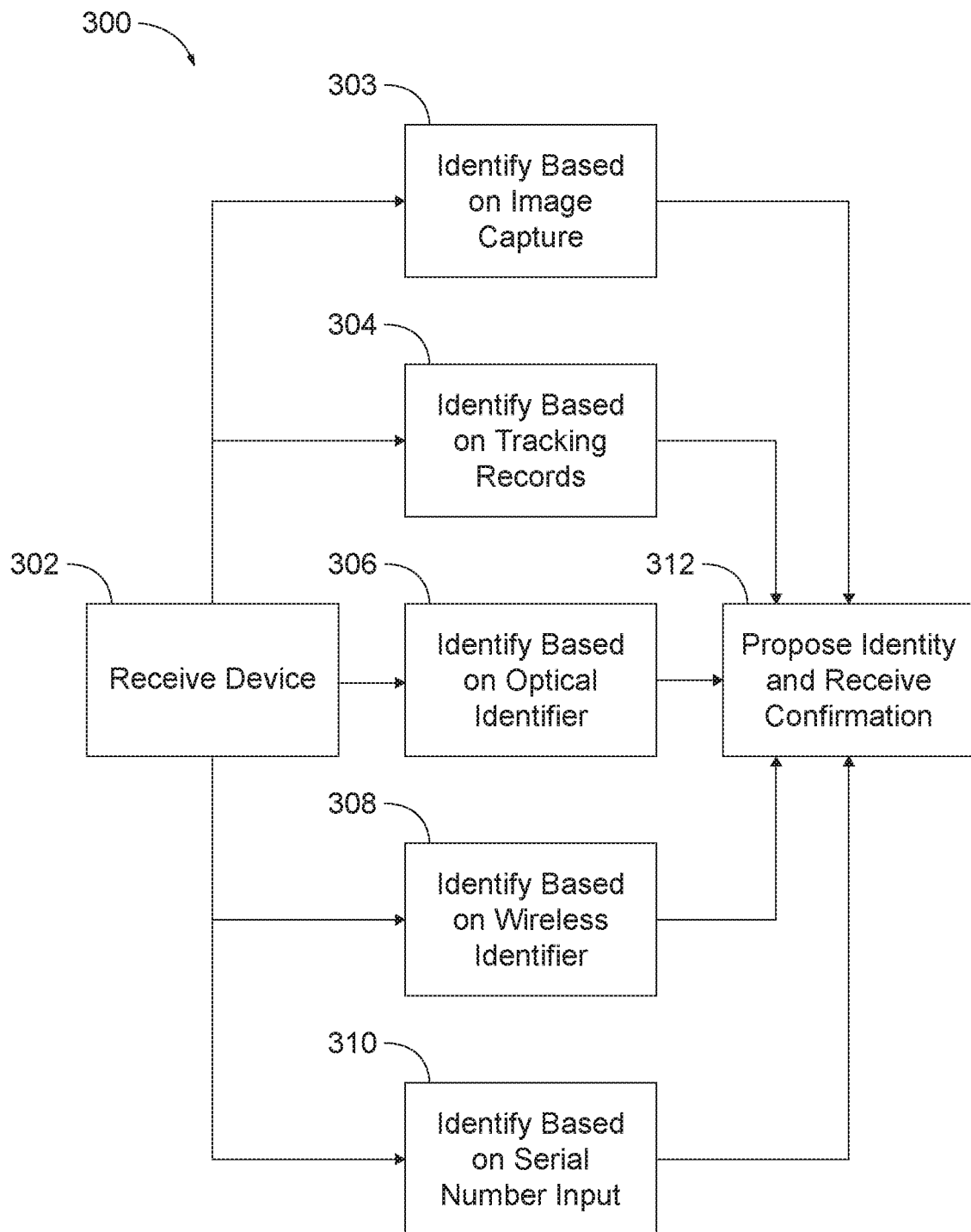
FIG. 4 depicts an exemplary set of steps that may be performed by a sterilization system such as that shown in FIG. 1 to automatically identify a medical device.

While manual identification of medical devices by users of system (10) may be accurate in some cases, automatic identification may further mitigate the risk of human error or equipment error resulting in misidentification of a medical device. The identity of a medical device may vary by implementation but could include one or more of a device type (e.g., an endoscope, a cutting instrument, a suction instrument, etc.), a device manufacturer, a semi-unique device model number, a unique device serial number, or other information. FIG. 4 shows an exemplary set of steps (300) that may be performed by or with system (10) to automatically determine the identity of a medical device. When a medical device is received (block 302) by a user of a device of system (10), such as sterilizing cabinet (100) or user device (108), various options may be available for identifying the medical device using the features and capabilities of system (10).

As an example, a user of sterilizing cabinet (100) may identify (block 303) the medical device based upon an image capture of the medical device, portions of the medical device, or identifying symbols, images, or text of the medical device. Image capture may be performed by interacting with features that are available to the device in use, such as reader (166) of sterilizing cabinet (100) or an alternate input of user device (108). This could include, for example, an image capture device capturing image data of a profile of the entire medical device and identifying it using an image analysis process; capturing image data of an end effector or other portion of the medical device and identifying it using an image analysis process; capturing image data of a serial number or model number present on the medical device, parsing the serial number or model number into text, and then identifying the medical device directly or using a device lookup table that is locally stored, or stored on server (106), stored in sterility guide database (110), or stored on another device or server; capturing image data of a barcode, QR code, or other visual identifier that encodes or otherwise represents data, and using that data to identify the medical device using the device lookup table; and other similar processes.

By way of further example only, sterilizing cabinet (100) may automatically identify (block 303) the medical device using advanced optical analysis, including but not limited to Fourier Transform Infrared Spectroscopy. As yet another merely illustrative example, sterilizing cabinet (100) may automatically identify (block 303) the medical device using mechanical sensing, including but not limited to weight plus dynamic dosing or loading response characteristics (e.g., pressure/peroxide concentration profiles). Various suitable hardware components and algorithms that may be used to provide automated identification (block 303) of the medical device by sterilizing cabinet (100) will be apparent to those skilled in the art in view of the teachings herein.

A successful identification (block 303) of the medical device based on image capture may be used, by itself or in combination with the results of other attempts at identification, to propose (block 312) a medical device identity to a user and receive confirmation from the user that the medical device was correctly identified, as will be described in more detail below.

As another example, a user of sterilizing cabinet (100) may identify (block 304) the medical device based upon device tracking records associated with the medical device and stored on server (106) or another device of system (10). A medical device or other material may be tracked throughout its lifetime to provide tracking information that may be used to locate lost or misplaced medical devices, determine current medical device inventory, audit processes related to handling medical devices before and after procedures, and other similar uses. Such tracking information may be generated by performing steps (314) such as those shown in FIG. 5. Whenever a medical device arrives (block 316) or departs (block 318) from a touch-point with a user having a device capable of interacting with system (10), such as sterilizing cabinet (100) or user device (108), the medical device may be identified (block 320) manually or automatically using some or all of the steps of FIG. 5, or another identification process. Once identified (block 320), system (10) may identify (block 322) a set of tracking records or create a new set of tracking records associated with the medical device that are stored in server (106), sterility guide database (110), or another server or location, and update (block 324) that set of tracking records to reflect the present arrival (block 316) or departure (block 318) of the medical device from the current touchpoint.

Information added to tracking records when they are updated (block 324) may include, when a device is arriving (block 316), the location the device arrived at, the location the device originated from, the time of arrival, a user that received the device upon arrival, the condition of the device upon arrival (e.g., new, used, sterile, non-sterile), any processes or procedures to be performed on or with the device while at the current location, a future destination of the device, and other similar information. When a device is departing (block 318), updated (block 324) information may include the location the device is departing from, the location the device is departing to, the time of departure, a user that received the device when it departed, the condition of the device upon departure (e.g., new, used, sterile, non-sterile), any processes or procedures performed on the device at the location it is departing from, and other similar information.

Returning to FIG. 4, such tracking information may be used to determine the identity (block 304) of a device that is arriving at a location such as sterilizing cabinet (100) or user device (108). For example, tracking information associated with Medical Device X may indicate that the device departed Procedure Room A at 1:00 PM and is being routed to Sterilizing Cabinet B by Technician C. Technician D, located at Sterilizing Cabinet B, may receive an unidentified medical device at 1:15 PM from Technician C. Technician D, using Sterilizing Cabinet B, may access tracking information and identify (block 304) the medical device as Medical Device X based upon the fact that it arrived with Technician C, at its intended location Sterilizing Cabinet B, within a reasonable time frame (e.g., 15 minutes) of its departure from Procedure Room A. Other data that may be stored and created as part of the tracking information, and other methods for using such data to identify (block 304) a medical device will be apparent to one skilled in the art in view of the teachings herein.

As another example, as has already been described in some detail in relation to identifying (block 303) a medical device based on image capture, a user of sterilizing cabinet (100) may identify (block 306) the medical device based upon an optical identifier. Where sterilizing cabinet (100) or user device (108) is capable of capturing and interpreting optical identifiers (e.g., with reader (166) or an alternate input of user device (108)), a unique or semi-unique optical identifier may be placed on the medical device that may be captured and checked against a record lookup table on server (106) or sterility guide database (110) to identify the device. This could include using an optical scanner to capture a barcode, QR code, or other visual marking intended to be captured by the optical scanner and configured to encode or otherwise indicate data that may be used to identify the device directly or using the record lookup table.

As another example, a user of sterilizing cabinet (100) may identify (block 308) the medical device based upon a wireless identifier. Where sterilizing cabinet (100) or user device (108) is capable of capturing and interpreting wireless identifiers (e.g., with reader (166) or alternate input (194)), a unique or semi-unique wireless identifier may be placed on the medical device that may be captured and checked against the record lookup table to identify the device. This could include using an RFID transceiver and RFID chip, a Bluetooth Transceiver and beacon, an NFC transceiver and beacon, a Wi-Fi transceiver and Wi-Fi antenna, or other wireless communication device combinations to wirelessly communicate data between the sterilizing cabinet (100) and the chip, beacon, or other device placed on or within, or transported with the medical device. Data provided from the medical device to the sterilizing cabinet (100) may then be used to identify the medical device directly or using the record lookup table.

As another example, a user of sterilizing cabinet (100) may identify (block 310) the medical device based upon a serial number or other numeric identifier input. A numeric identifier may be input for a medical device by, for example, hand-keying with a keyboard or touch screen display (160), or by connecting a power or data port of the medical device to the sterilizing cabinet (100) in order to automatically retrieve the numeric identifier from a chip or memory of the medical device. As with prior examples, the numeric identifier may be used to identify the medical device directly or using the record lookup table.

As has been mentioned, after one or more medical device identifications are made, the sterilizing cabinet (100), user device (108), or other device performing the identifications may propose (block 312) an identity for the medical device to a user via a display or other user interface; and receive confirmation from the user of the device identity via a keyboard, mouse, touch screen display (160), or other user interface available to that device. Where only a single identification method is used, or multiple identification methods are used and determine a common identity, only one option may be proposed (block 312) to a user.

Where multiple identification methods are used, and multiple identities are determined, each option may be proposed (block 312) to a user; or a most likely identity may be determined and proposed (block 312) to the user, with other identities being discarded or only proposed (block 312) if the user does not confirm the first identity. In some implementations, identities may be proposed (block 312) and displayed with additional information such as a confidence level (e.g., high or low, percentage based), a source of the identification (e.g., identified by tracking records and optical identifier), or other information that is available to system (10) and that may aid user in confirming the medical device identity. Confidence levels and other determinations relating to the accuracy of a determined identity may be configured by an administrator of the system and based upon the source of the identification (e.g., manually input serial number may be a lower confidence while automatically scanned optical identifier may be a higher confidence), and adjusted over time based upon real world use of the system (e.g., raising the level of confidence in manually input serial numbers after they are determined to be highly accurate).

IV. Exemplary Method for Verifying Medical Instrument Sterilization Compatibility Different medical devices may have different requirements for sterilization, and so sterilizing cabinet (100) is configurable to perform sterilization procedures having different characteristics. The characteristics of a sterilization procedure may be manually configured or may be selected based upon a selected sterilization cycle (block 200). These characteristics may include such factors as precise placement of a medical device within the sterilizing cabinet (100) (e.g., top shelf, bottom shelf, middle of shelf), number of medical devices that may be placed within the sterilizing cabinet (100) at one time, particular sterilant to use during a procedure, the total time of the procedure, a number of different stages of a procedure and a time for each stage, an appropriate biological indicator to use and biological indicator placement, and other similar characteristics. A sterilization cycle may combine one or more of these characteristics or others into a pre-configured process that may be selected to be performed by the sterilizing cabinet (100) based upon a single user selection.

Whether a sterilization process is manually configured or configured by the selection (block 200) of a sterilization cycle to be performed, there is a possibility for user error resulting in an unsterilized medical device returning to service, or a sterilized medical device being unnecessarily re-sterilized, if a user misunderstands the selection process or misidentifies the medical device and performs a sterilization procedure that is not adequate to completely sterilize the medical device. Even where there is no true user error (e.g., the user makes appropriate selections based upon their training and the medical device involved), some medical devices may not be verifiably compatible with certain sterilization cycles or sterilizing cabinets (100), even though users and providers believe they are.

For example, an older version of a medical device may have been tested and verified as compatible with one or more sterilization cycles of sterilizing cabinet (100). A newer version of the medical device may be released that is seemingly identical to the older version, but due to changes on the interior of the device that are imperceptible to the end user, the newer version of the medical device may be incompatible with one or more cycles of sterilizing cabinet (100).

To address such concerns, the sterility guide database (110) stores a number of records associating medical devices with sterilization equipment and processes, such as the sterilization cycles of sterilizing cabinet (100); and provides an indication of compatibility. The sterility guide database (110) may be populated with data by a single party responsible for maintaining it (e.g., a manufacturer of sterilizing cabinets or a medical safety association); or may be populated by multiple users of the sterility guide database (e.g., medical device manufacturers). Data may be created and populated based upon targeted testing of new medical devices, such as focused testing on new devices as they are released to determine whether they are successfully sterilized by a device or procedure; or may be created and populated based upon similarities to prior devices, simulation models, or other techniques. In effect, the sterility guide database (110) may be accessed by a user to provide an assurance that a particular medical device is sterile after a procedure.

Figure 5:
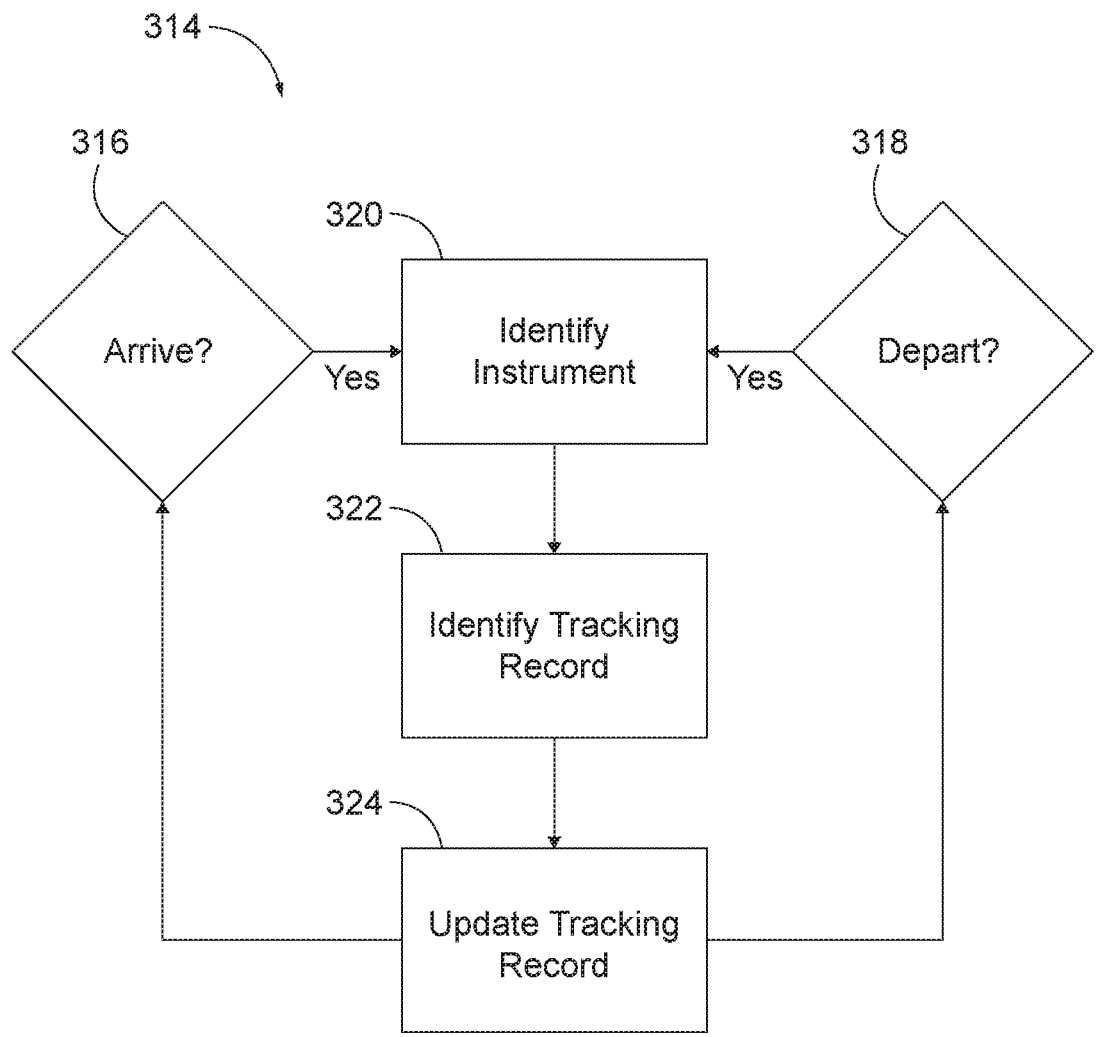
FIG. 5 depicts an exemplary set of steps that may be performed by a sterilization system such as that shown in FIG. 1 to track medical devices throughout their lifecycle.
Figure 6:
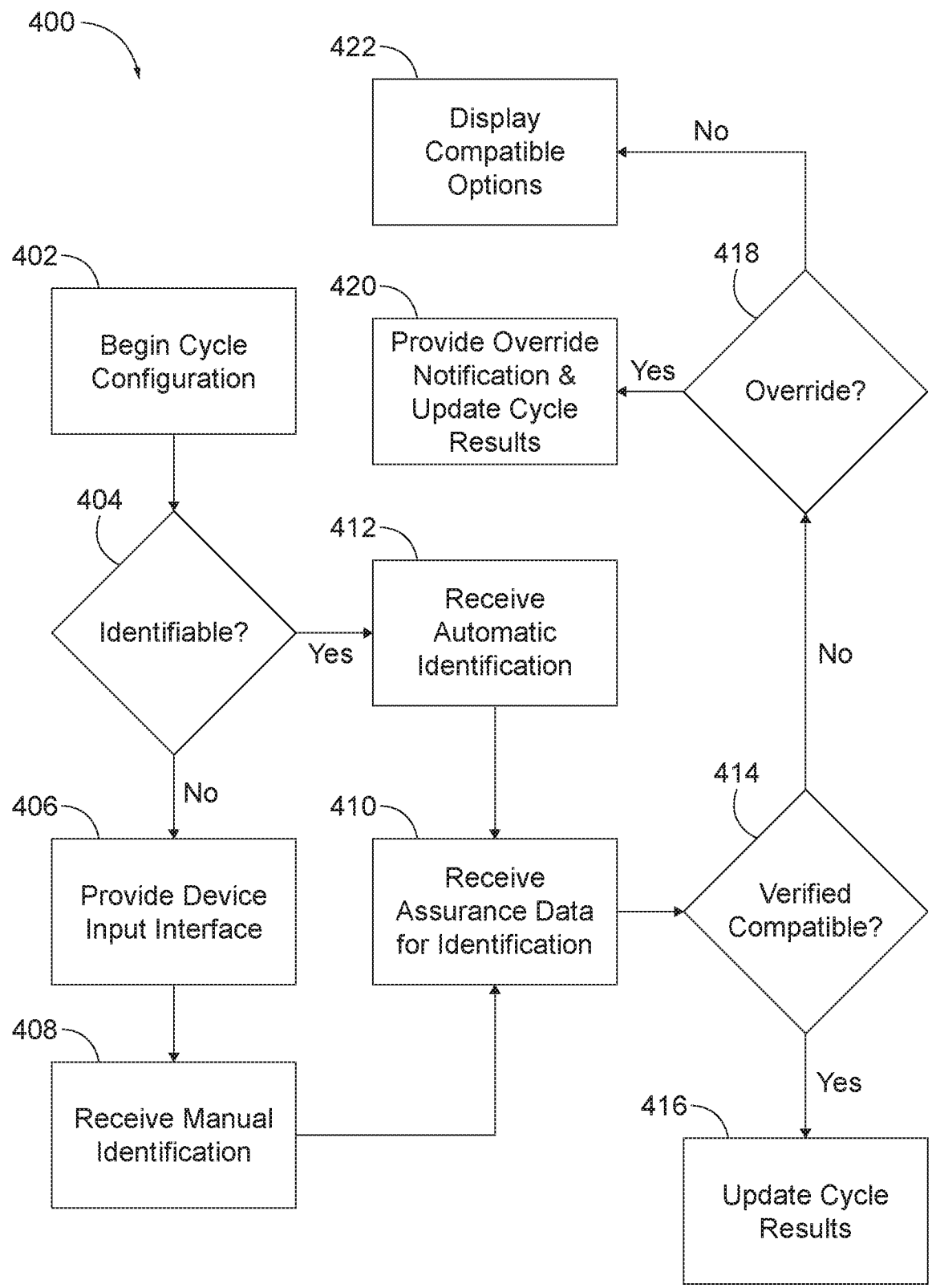
FIG. 6 depicts an exemplary set of steps that may be performed by a sterilization system such as that shown in FIG. 1 to automatically verify the compatibility of a medical device with one or more components of the system.

FIG. 6 shows a set of exemplary steps (400) that may be performed with system (10) to verify the compatibility of a sterilization procedure with a particular medical device using the sterility guide database (110). When a non-sterile medical device is received, a user may begin (block 402) configuring a sterilization cycle for that medical device using the sterilizing cabinet (100). While the steps of FIG. 6 may be performed at the beginning (block 402) of configuration of a sterilization cycle, they may alternatively or additionally be performed after the performance of a sterilization cycle as may be desired in some implementations. If the medical device is identifiable (block 404), using steps such as those shown in FIG. 5, the sterilizing cabinet (100) may receive (block 412) the device identification automatically. If the device is not identifiable (block 404), the sterilizing cabinet (100) may provide (block 406) a device input interface to a user and receive (block 408) a manual identification of the medical device from the user.

The device input interface may include, for example, a set of selection menus, drop down menus, buttons, boxes, or other interface elements that allow a user to browse through a list of medical devices to identify the medical device. This could include, for example, allowing a user to select a manufacturer from a menu and providing a list of device types provided by that manufacturer, allowing a user to select a device type and providing a list of device models included in that device type, and allowing a user to select a device model. This could also include providing a user with a series of questions about the form (e.g., "What is the total length of the device?"), features (e.g., "Does the device have a battery?"), or other aspects of the medical device that are structured to narrow down and identify the device. The interface may be provided through touch screen display (160) or otherwise.

Once the medical device is identified, whether automatically (block 412) or manually (block 408), the sterilizing cabinet (100) may access the sterility guide database (100) and receive (block 410) a set of assurance data associated with the medical device. The set of assurance data may indicate one or more sterilization cycles, sterilizing cabinets such as sterilizing cabinet (100), sterilants, or other devices or processes that have been verified as being compatible with the medical device. Sterilizing cabinet (100) may then verify (block 414) the compatibility of its available sterilization cycles or other features; and, where the user performs a verified compatible sterilization cycle, update (block 416) the sterilization cycle results for that sterilization cycle. Sterilization cycle results are a set of records stored on server (106) or another device of system (10) that indicate, for each sterilization cycle performed on that device, the characteristics of the cycle, the medical devices included in the cycle, and the results of the cycle as indicated by a biological indicator used with the cycle. The updated (block 416) cycle results may additionally include information from the sterility guide database (110) indicating that the performed cycle has been assured as being compatible with the medical device, which provides further assurance that the medical is sterile after the cycle.

Where a user selects a sterilization cycle or process that cannot be verified (block 414) as being compatible with the medical device, sterilizing cabinet (100) may present the user with a warning or notification of the lack of assurance; and ask the user to override (block 418) the warning to continue performing the possibly incompatible sterilization cycle. Where the user overrides (block 418) the notification and performs the possibly incompatible sterilization cycle, the sterilizing cabinet (100) may provide (block 420) an override notification and update the sterilization cycle results. The override notification may be configured to be provided to the user performing the override, to users responsible for the sterilizing cabinet (100) itself or the section of the hospital where it is present, to users responsible for sterilization procedures for the hospital generally, or other users as may be desired and configured by an administrator of system (10). Sterilization cycle results may be updated to reflect that, while a biological indicator used with the sterilization cycle may have indicated that it was successful, system (10) was unable to provide an assurance that the medical device was compatible with the performed cycle and successfully sterilized, based upon the information available via sterility guide database (110).

Where the user does not override (block 418) the notification of possible incompatibility, the sterilizing cabinet (100) may display (block 422) one or more options for sterilizing the medical device for which assurance of compatibility is available. This could include, for example, selecting a different sterilization cycle on sterilizing cabinet (100), or transporting the medical device to another type of sterilizing cabinet or device.

FIGS. 7-13 show screenshots of exemplary interfaces that may be displayed to a user via touch screen display (160) of sterilizing cabinet (100), or via another display or device, during one or more of the steps of FIG. 6, including during configuration of a sterilization cycle to be performed with a medical device.

Figure 7:
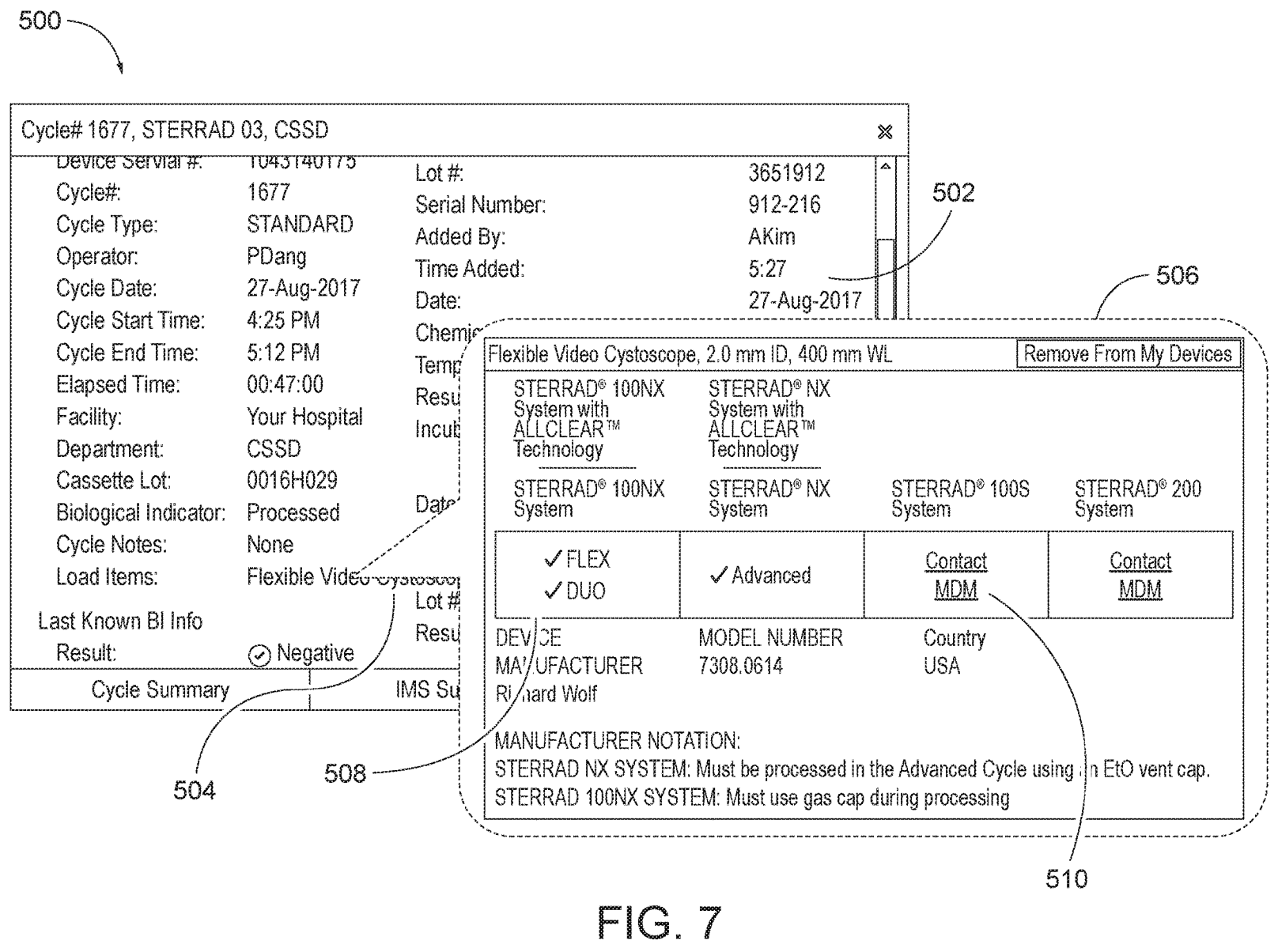

FIG. 7 shows an interface (500) that displays a set of cycle information (502) associated with a sterilization cycle that is configured and ready to be performed, or that has been performed on sterilizing cabinet (100). Set of cycle information (502) comprises a load description (504) indicating one or more medical devices that are part of the load of the sterilization cycle. An assurance window (506) may be displayed by, for example, hovering over or clicking on a medical device shown in load description (504). Assurance window (506) comprises a list of sterilizing cabinets or devices and provides an assurance indication (508) for one or more sterilization cycles available to those sterilizing cabinets, based upon assurance data received (block 410) for the medical device. Assurance window (506) may also provide a lack of assurance indication (510) for one or more sterilizing cabinets (100) for which the assurance data received (block 410) does not provide assurance of compatibility. Lack assurance indication (510) may comprise instructions for seeking or requesting assurance; or may include a clickable button or other interactive feature that may automatically request assurance from a party responsible for maintaining the sterility guide database (100).

FIG. 8 shows an interface (512) that displays a more detailed view of one or more medical devices present in a sterilization cycle load (514). Interface (512) shows a set of rows showing additional information on a first medical device (516) and a second medical device (518) such as device manufacturer, device name, and model number, and a set of columns providing an assurance indication (520) for one or more sterilization cycles available to those medical devices. Interface (512) may also provide a lack of assurance indication where appropriate.

Figure 9:
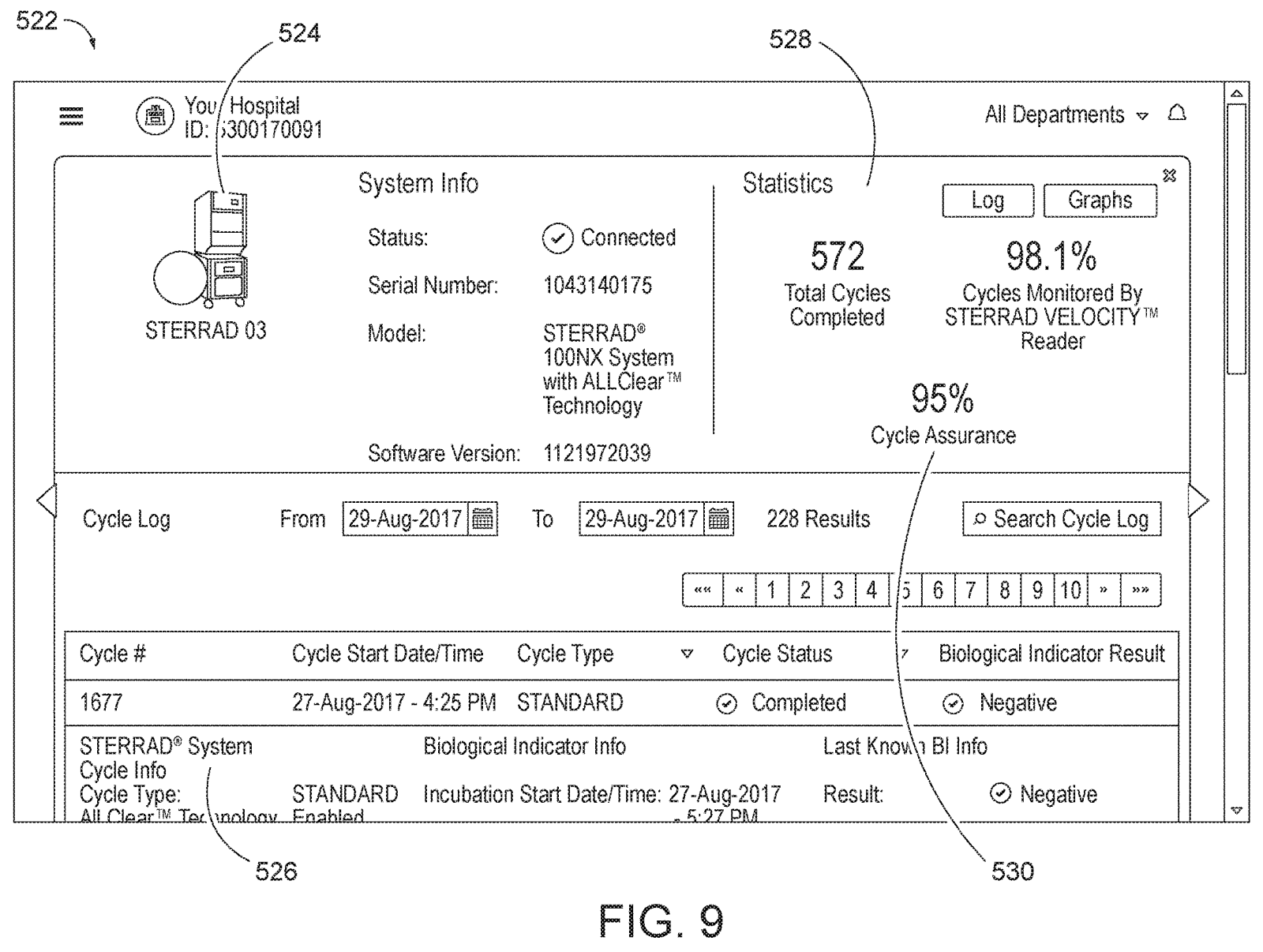

FIG. 9 shows an interface (522) that displays a view of information associated with sterilization cycles (526) performed with a sterilization device (524). Interface (524) also shows a device cycle summary (528) comprising a set of aggregate information based upon information associated with sterilization cycles (526), and an assurance rate (530) indicating an aggregate percentage of cycles that were verified (block 414) as compatible rather than being overridden (block 418) and performed.

Figure 10:
FIG. 10 depicts an exemplary interface for configuring one or more alerts associated with incompatible sterilization cycles.

FIG. 10 shows an interface (532) that displays various notification options for different types of alerts (536) that may be provided by system (10) and different forms of communication (534) that may be used by system (10) to provide the types of alerts (536) to one or more users of system (10). An administrator of system (10) may use interface (532) to configure various alert scenarios, including configuring system (10) to provide alerts to one or more users or types of users based upon an indication of an unverified sterilization cycle being performed (538). Such an alert may be generated and communicated to users based upon the configured forms of communication (534) when a user overrides (block 418) a notification that a sterilization cycle cannot be assured as being compatible with a medical device, as part of providing (block 420) override notification.

Figure 11:
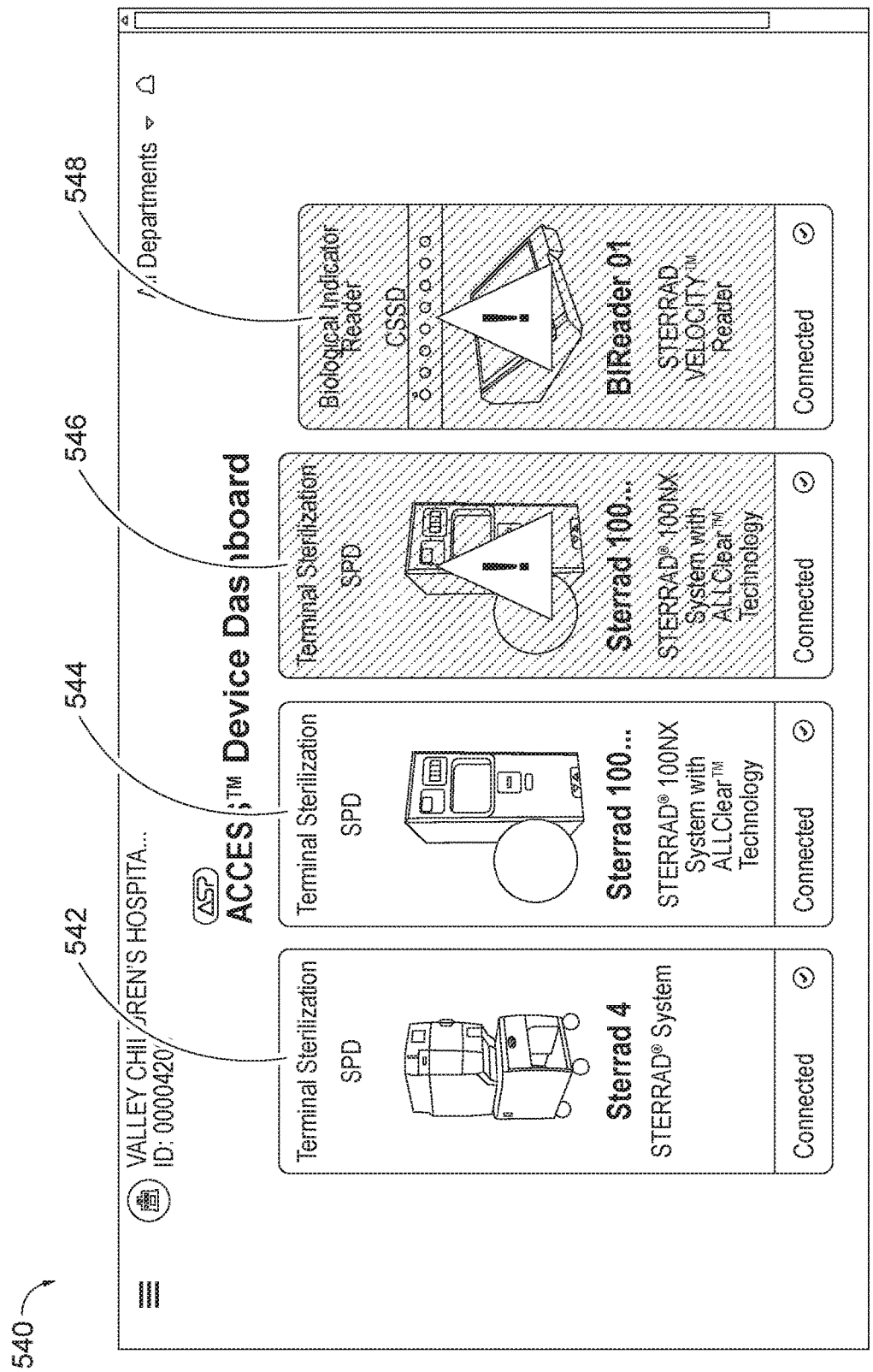
FIG. 11 depicts an exemplary interface for choosing devices based upon their compatibility with a medical device.

FIG. 11 shows an interface (540) that displays a set of sterilization devices available to a user (e.g., a device the user is presently interacting with, devices available in the same room, devices available in other areas of a hospital)

and whether they have been assured as being compatible with the medical device for which the sterilization cycle will be performed. As can be seen, a first sterilizing cabinet (542) and a second sterilizing cabinet (544) appear in a manner that indicates they have compatible sterilization cycles that may be used with the medical device based upon an assurance of compatibility received (block 410) from the sterility guide database (110). Conversely, a third sterilizing cabinet (546) and a sterilizing device (548) appear in a manner that indicates they have not been assured as compatible with the medical device, based upon the received (block 410) assurance data lacking any indication of compatibility with the medical device. A user selection of the third sterilizing cabinet (546) may result in interface (540) presenting a warning indicating that the user must override (block 418) the unassured sterilization cycle to continue.

FIG. 12 shows an interface (550) displaying a hospital level instrumentation status (552) showing information on a plurality of medical devices currently in use at a particular hospital, building, or site, and their assurance level for sterilizing cabinets and sterilization cycles available at that same locale. A set of medical devices are displayed in rows, including a first medical device (554) and a second medical device (556), and a first column presents information associated with those devices such as device manufacturer, device name, model number, and manufacturer's notes related to the device. A set of columns (560) show for each sterilizing cabinet a set of sterilization cycles that are compatible with each of the first medical device (554) and the second medical device (556). Interface (550) may be used by an administrator or person responsible for medical device sterilization to easily view each medical device currently in use at the hospital, and the compatibility assured sterilization resources available for each medical device, to verify that all presently used medical devices have some level of compatibility assured sterilization available.

Figure 13:
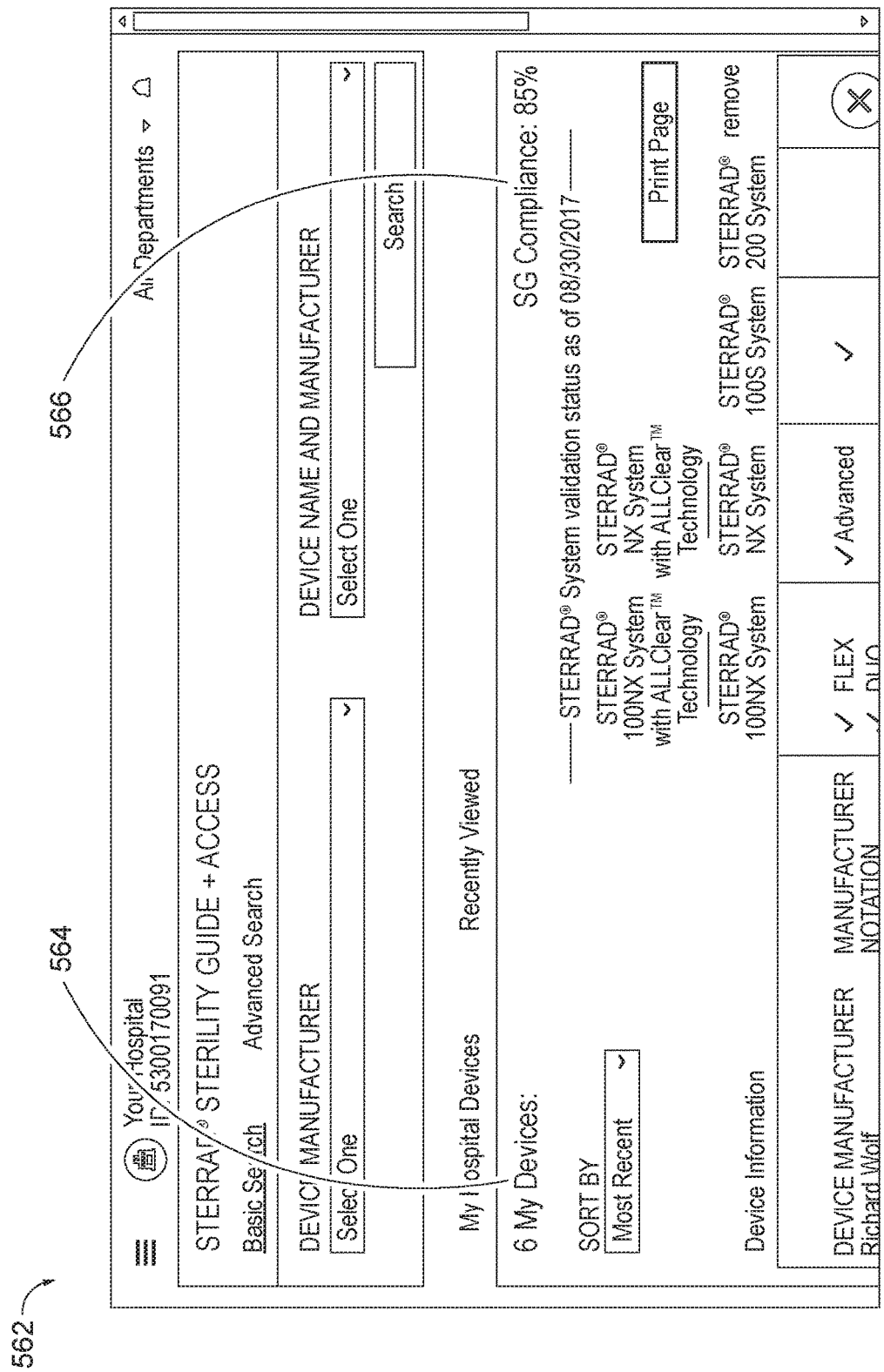
FIG. 13 depicts an exemplary interface for viewing an overall compatibility level.
Figure 14:
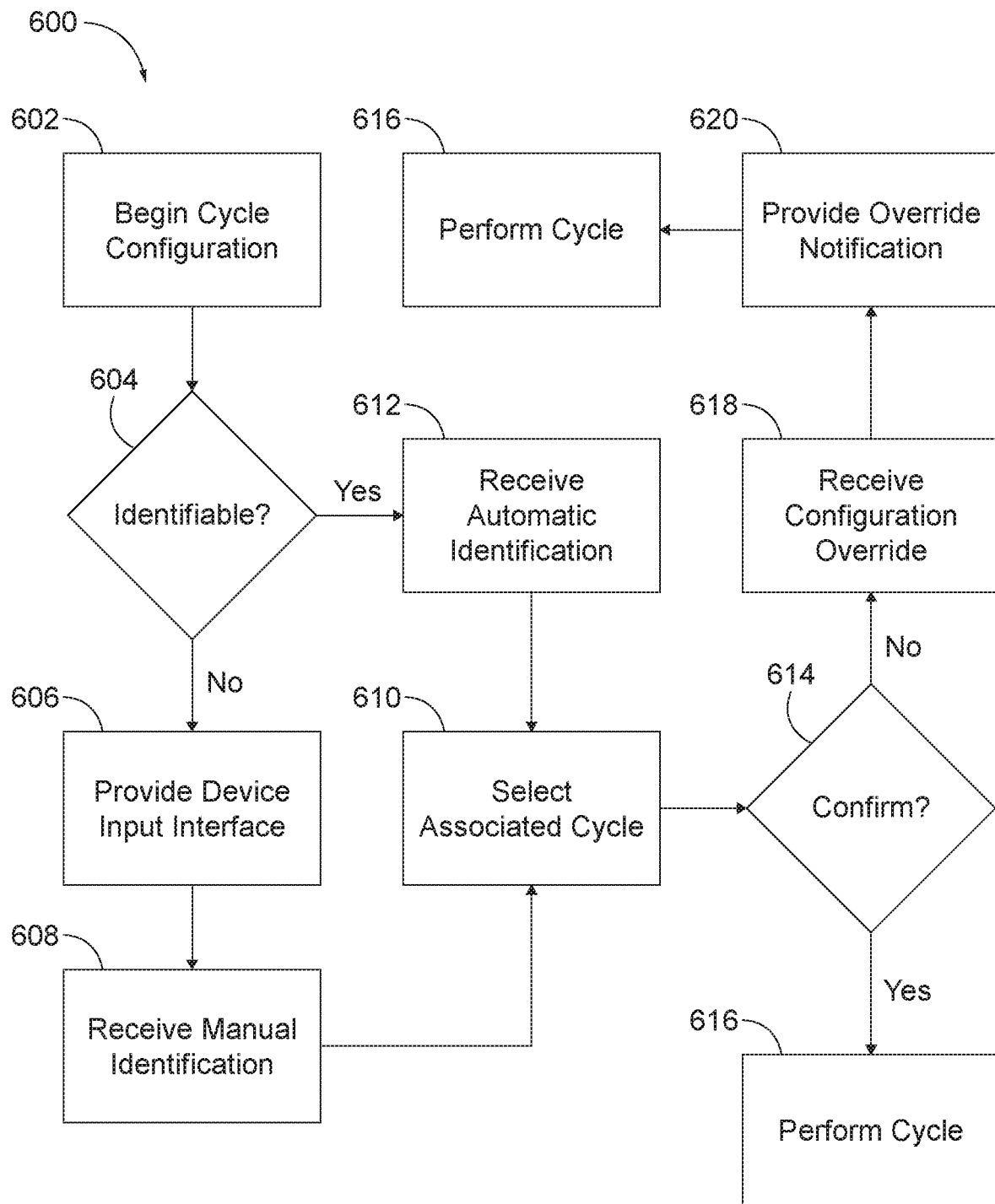
FIG. 14 depicts an exemplary set of steps that may be performed by a sterilization system such as that shown in FIG. 1 to automatically select and configure an appropriate sterilization cycle for a device.

FIG. 13 shows an interface (562) displaying an alternate view of some of the data shown in FIG. 12. The alternate view of interface (562) displays information on a set of medical devices (564) currently in use at a particular hospital, site, or other location, as well as the compatibility assurances for each medical device as discussed in the context of FIG. 12; and additionally shows a hospital assurance rate (566). Hospital assurance rate (566) may indicate a percentage of the set of medical devices (564) that have some assured compatibility with sterilizing devices present at the hospital; or may indicate an aggregate percentage of compatibility assured sterilization cycles performed at the hospital during a period of time. Additional interfaces and variations on the described interfaces exist and will be apparent to one skilled in the art in view of the teachings herein.

V. Exemplary Method for Automatic Sterilization Cycle Selection

While the disclosed systems and methods mitigate risks associated sterilization procedures and provide assurances of successful sterilization, the below described method may be implemented in system (10) individually or in combination with these other techniques to further reduce the chance of error. FIG. 15 shows an exemplary set of steps (600) that may be performed by or with system (10) to automatically configure a sterilizing cabinet such as sterilizing cabinet (100).

When a user receives a medical device at sterilizing cabinet (100) and begins (block 602) the sterilization cycle configuration, the medical device may be identified (block 604) by performing steps such as those shown in FIG. 5. If the medical device is successfully identified (block 604) and confirmed, the sterilizing cabinet (100) may automatically receive the medical device identity. If the device is not identifiable (block 604), the sterilizing cabinet (100) may provide (block 606) a device input interface to a user; and receive (block 608) a manual identification of the medical device from the user.

The device input interface may include, for example, a set of selection menus, drop down menus, buttons, boxes, or other interface elements that allow a user to browse through a list of medical devices in order to identify the medical device. This could include, for example, allowing a user to select a manufacturer from a menu and providing a list of device types provided by that manufacturer, allowing a user to select a device type and providing a list of device models included in that device type, and allowing a user to select a device model. This could also include providing a user with a series of questions about the form (e.g., "What is the total length of the device?"), features (e.g., "Does the device have a battery?"), or other aspects of the medical device that are structured to narrow down and identify the device. The interface may be provided through touch screen display (160) or otherwise.

Once the medical device is identified, whether automatically (block 612) or manually (block 608), the sterilizing cabinet (100) may select a compatible sterilization cycle based upon the medical device identity. This could include, for example, accessing server (106) to identify compatible sterilization cycles associated with the medical device, accessing the sterility guide database (110) to identify compatibility assured sterilization cycles associated with the medical device, or both. In some cases, the sterilizing cabinet (100) may also select (block 610) an associated cycle based entirely upon or in part upon tracking information provided with the medical device upon arrival, as has been described.

In some scenarios, the identified medical device may not be found in the sterility guide database (110), yet the user reasonably believes that the medical device is in fact compatible with sterilizing cabinet (100) (e.g., due to a notice published by the manufacturer of the medical device or a notice published by the manufacturer of sterilizing cabinet (100), etc.). In some such scenarios, sterilizing cabinet (100) may present the user with a user interface that enables the user to update the sterility guide database (110) to include that medical device. Thus, the next time a user tries to sterilize the same medical device in sterilizing cabinet (100), a check of sterility guide database (110) will confirm that the medical device is compatible with sterilizing cabinet (100). As another variation of this concept, sterilizing cabinet (100) may present the user with a user interface that enables the user to compile separate listings of medical devices that are compatible with sterilizing cabinet (100). Such separate listings may be stored elsewhere (i.e., not in sterility guide database (110)); or may be stored in sterility guide database (110) (e.g., in a listing that is separate from manufacturer-defined listing(s)). In some such versions, sterilizing cabinet (100) may first check the manufacturer-defined listing(s) in sterility guide database (110); and if the medical device is not found in the manufacturer-defined listing(s), then check the user-defined listing(s).

Regardless of whether the medical device identification is performed manually (block 608) or automatically (block 612), the selected (block 610) sterilization cycle may be presented to a user via the sterilizing cabinet (100) for confirmation (block 614), and, where a user confirms that the selected (block 610) cycle should be performed, the cycle may be automatically performed (block 616). Where the user does not wish to proceed with the selected (block 610) cycle and does not confirm (block 614) the sterilization cycle, the sterilizing cabinet (100) may receive (block 618) a configuration override that causes a different sterilization cycle to be selected; or that modifies one or more characteristics of the selected sterilization cycle. The sterilizing cabinet (100) may provide (block 620) an override notification, similar to prior discussion of providing (block 420) override notifications; and may perform (block 616) the override sterilization cycle.

System (10) and sterilizing cabinet (100) may be configured to perform steps such as those shown in FIG. 6, or steps such as those shown in FIG. 15, or both, as may be desirable. In implementations performing steps such as those shown in both FIG. 6 and FIG. 15, such steps may be performed in series or in parallel as may be desirable. For example, where the sterilization cycle is selected (610) based upon data from the sterility guide database (110), the configured cycle may be inherently associated with an assurance of compatibility with the medical device from the sterility guide database (110). Such an assurance could be presented in addition to other information when a user is prompted to confirm (block 614) the selected (block 610) cycle, and cycle results may be updated (block 416) with the assurance after the cycle is performed (block 616) and the cycle results are generated.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A device usable with a sterilization system for a medical device, the device comprising: (a) a processor and a memory; (b) a communication device; (c) a user input; and (d) a display; wherein the processor is configured to: (i) receive a device indicator associated with the medical device, (ii) access a set of medical device records and determine an identity of the medical device based upon an association of the device indicator with the set of medical device records, (iii) configure at least one risk mitigation process based upon the identity of the medical device, and (iv) configure a sterilization cycle to be performed on the medical device based upon the at least one risk mitigation process.

Example 2

The device of Example 1, wherein the device is a sterilizing cabinet; wherein the communication device is a wireless transceiver configured to be connected to the sterilization system via a wireless communication network; wherein the user input comprises a touchscreen and an optical reader; wherein the identifier is a model number associated with a unique description of the medical device; wherein the identity is the unique description of the medical device.

Example 3

The device of any one or more of Examples 1 through 2, wherein the device indicator is a set of device tracking information received from the sterilization system; wherein the set of device tracking information indicates an in-transit medical device leaving from an origin and having a destination of the device; wherein the set of medical device records associate the in-transit medical device with the identity of the medical device; wherein the processor is further configured to determine that the medical device is the in-transit medical device.

Example 4

The device of any one or more of Examples 1 through 3, wherein the user input comprises an optical reader that is operable to read data encoded in an optical identifier; wherein the optical reader is configured to receive the device indicator after the optical reader reads the optical identifier; wherein the set of medical device records associate the optical identifier with the identity of the medical device.

Example 5

The device of any one or more of Examples 1 through 4, wherein the user input comprises a text input that is operable to provide a text identifier to the device; wherein the text input is configured to receive the device indicator as the text identifier; wherein the set of medical device records associate the text identifier with the identity of the medical device.

Example 6

The device of any one or more of Examples 1 through 5, wherein the processor is further configured to: (i) after the identity of the medical device is determined, display the identity to a user via the display, (ii) receive an identity response from a user via the user interface, (iii) where the identity response indicates that the identity is not correct, provide a manual device input interface via the display, wherein the manual device input interface comprises a set of prompts for additional information operable by the user to determine a new identity of the medical device, and (iv) configure the at least one risk mitigation process based upon the new identity instead of the identity.

Example 7

The device of any one or more of Examples 1 through 6, wherein the at least one risk mitigation process comprises a compatibility assurance process, wherein the compatibility assurance process is configured to cause the processor to: (i) determine a sterilizing cabinet identifier associated with the sterilization cycle, (ii) determine a sterilization cycle type associated with the sterilization cycle, and (iii) receive a device assurance indicator from a sterility guide database of the sterilization system based upon the sterilizing cabinet identifier, the sterilization cycle type, and the identity of the medical device, wherein the device assurance indicator indicates whether the medical device is compatible with a sterilizing cabinet associated with the sterilizing cabinet identifier and a sterilization cycle associated with the sterilization cycle type.

Example 8

The device of Example 7, wherein the processor is further configured to: (i) determine a set of sterilizing cabinets that are present in the sterilization system, (ii) determine, for each sterilizing cabinet in the set of sterilizing cabinets, a set of sterilization cycles that each sterilizing cabinet is capable of performing, (iii) receive a set of device assurance indicators for each sterilizing cabinet of the set of sterilizing cabinets from the sterility guide database and determine a set of compatible sterilization cycle options based upon the set of device assurance indicators, (iv) display the set of compatible sterilization cycle options via the display, (v) receive a selection via the user input, wherein the selection is associated with an option of the set of compatible sterilization cycle options, and (vi) configure the sterilization cycle based upon the selection.

Example 9

The device of any one or more of Examples 7 through 8, wherein the processor is further configured to, when the device assurance indicator indicates that the medical device is compatible: (i) indicate via the display that the sterilization cycle is compatible with the medical device, and (ii) upon completion of the sterilization cycle, add a compatibility assured indicator to a cycle result dataset, wherein the cycle result dataset describes the performance of the sterilization cycle and the compatibility assured indicator indicates that the medical device was compatible with the sterilization cycle.

Example 10

The device of Example 9, wherein the processor is further configured to, when the device assurance indicator indicates that the medical device is not assured as compatible: (i) display via the display a compatibility warning that indicates the sterilization cycle is not assured as compatible with the medical device, (ii) receive a confirmation via the user input to override the compatibility warning and proceed with the sterilization cycle, (iii) provide an unverified cycle alert via the communication device as an electronic message to one or more recipients, and (iv) upon completion of the sterilization cycle, add an assurance warning indicator to a cycle result dataset, wherein the cycle result dataset describes the performance of the sterilization cycle and the compatibility assured indicator indicates that the medical device was not assured as compatible with the sterilization cycle.

Example 11

The device of any one or more of Examples 7 through 10, wherein the processor is further configured to cause a device cycle summary interface to display via the display, wherein the device cycle summary interface comprises: (A) a sterilizing cabinet descriptor, (B) a list of cycle results for sterilization cycles performed on a sterilizing cabinet associated with the sterilizing cabinet descriptor, and (C) an assurance rate indicating the portion of the list of cycle results associated with a compatible device assurance indicator.

Example 12

The device of any one or more of Examples 7 through 11, wherein the processor is further configured to cause an instrumentation assurance summary interface to display via the display, wherein the instrumentation assurance summary interface comprises: (A) a set of medical device descriptors for each medical device in service at a location, (B) a set of sterilizing equipment descriptors for sterilizing devices in service at the location, (C) a set of assurance descriptors indicating which of the sterilizing devices in service at the location are assured as compatible for each medical device in service at the location, and (D) an assurance rate indicating whether any of the medical devices in service at the location are not compatible with any sterilizing devices in service at the location.

Example 13

The device of Example 12, wherein the instrumentation assurance summary interface further comprises a request assurance feature associated with an unverified medical device of the set of medical device descriptors; wherein the request assurance feature may be interacted with via the user interface to cause an electronic communication to be sent to a recipient associated with the sterility guide database; wherein the electronic communication describes the unverified medical device and the set of sterilizing equipment descriptors.

Example 14

The device of any one or more of Examples 1 through 13, wherein the at least one risk mitigation process comprises an automatic cycle selection, wherein the compatibility assurance process is configured to cause the processor to: (i) determine an approved cycle configuration based upon the identity of the medical device, and (ii) configure the sterilization cycle based upon the approved cycle configuration.

Example 15

The device of Example 14, wherein the approved cycle configuration is associated with a device assurance indicator, wherein the device assurance indicator is configured to be received from a sterility guide database based upon the identity of the medical device, wherein the device assurance indicator is further configured to indicate that the medical device is compatible with the sterilization cycle.

Example 16

A method for configuring a sterilization system to sterilize a medical device comprising the steps: (a) receiving a device indicator that is associated with the medical device; (b) accessing a set of medical device records; (c) determining an identity of the medical device based upon an associated of the device indicator with the set of medical device records; (d) configuring at least one risk mitigation process based upon the identity of the medical device; and (e) configuring a sterilization cycle to be performed on the medical device based upon the at least one risk mitigation process.

Example 17

The method of Example 16, wherein configuring the at least one risk mitigation process comprises the steps: (i) determining a sterilizing cabinet identifier associated with the sterilization cycle, (ii) determining a sterilization cycle type associated with the sterilization cycle, and (iii) receiving a device assurance indicator from a sterility guide database of the sterilization system based upon the sterilizing cabinet identifier, the sterilization cycle type, and the identity of the medical device, and wherein the device assurance indicator indicates whether the medical device is compatible with a sterilizing cabinet associated with the sterilizing cabinet identifier and a sterilization cycle associated with the sterilization cycle type.

Example 18

The method of Example 17, further comprising the steps: (a) determining a set of sterilizing cabinets that are present in the sterilization system; (b) determining for each sterilizing cabinet in the set of sterilizing cabinets, a set of sterilization cycles that each sterilizing cabinet is capable of performing; (c) receiving set of device assurance indicators for each sterilizing cabinet of the set of sterilizing cabinets from the sterility guide database and determine a set of compatible sterilization cycle options based upon the set of device assurance indicators; (d) displaying the set of compatible sterilization cycle options to a user of the sterilization system; (e) receiving a selection from the user, wherein the selection is associated with an option of the set of compatible sterilization cycle options; and (f) configuring the sterilization cycle based upon the selection.

Example 19

The method of any one or more of Examples 16 through 18, wherein configuring the at least one risk mitigation process comprises the steps: (i) accessing a database and retrieving a set of medical device records, (ii) determining an approved cycle configuration based upon the identity of the medical device and the set of medical device records, and (iii) configuring the sterilization cycle based upon the approved cycle configuration.

Example 20

A sterilization system comprising: (a) a sterilizing cabinet operable to perform a sterilization cycle on a medical device; (c) a sterility guide database comprising a set of assurance indicators, the set of assurance indicators indicating a plurality of sterilizing cabinets that have been assured as compatible with a plurality of medical devices; and (d) a communication hub configured to provide communication between the sterilizing cabinet and the sterility guide database; wherein the sterilizing cabinet is configured to: (i) receive a device indicator associated with the medical device, (ii) access a set of medical device records and determine an identity of the medical device based upon an association of the device indicator with the set of medical device records, (iii) determine a sterilizing cabinet identifier associated with the sterilizing cabinet and a sterilization cycle type associated with the sterilization cycle, (iv) receive an assurance indicator from the sterility guide database based upon the sterilizing cabinet identifier, the sterilization cycle type, and the identity of the medical device, (v) configure the sterilization cycle to be performed on the medical device based upon the assurance indicator.

VII. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for configuring a sterilization system to sterilize a medical device comprising the steps:
    (a) receiving a device indicator that is associated with the medical device;
    (b) accessing a set of medical device records;
    (c) determining an identity of the medical device based upon an association of the device indicator with the set of medical device records;
    (d) configuring at least one risk mitigation process based upon the identity of the medical device; and
    (e) configuring a sterilization cycle to be performed on the medical device based upon the at least one risk mitigation process, wherein configuring the at least one risk mitigation process comprises the steps:
        (i) determining a sterilizing cabinet identifier associated with the sterilization cycle,
        (ii) determining a sterilization cycle type associated with the sterilization cycle, and
        (iii) receiving a device assurance indicator from a sterility guide database of the sterilization system based upon the sterilizing cabinet identifier, the sterilization cycle type, and the identity of the medical device, and
    wherein the device assurance indicator indicates whether the medical device is compatible with a sterilizing cabinet associated with the sterilizing cabinet identifier and a sterilization cycle associated with the sterilization cycle type.

2. The method of claim 1, further comprising the steps:
    (a) determining a set of sterilizing cabinets that are present in the sterilization system;

(b) determining for each sterilizing cabinet in the set of sterilizing cabinets, a set of sterilization cycles that each sterilizing cabinet is capable of performing;

(c) receiving a set of device assurance indicators for each sterilizing cabinet of the set of sterilizing cabinets from the sterility guide database and determine a set of compatible sterilization cycle options based upon the set of device assurance indicators;

(d) displaying the set of compatible sterilization cycle options to a user of the sterilization system;

(e) receiving a selection from the user, wherein the selection is associated with an option of the set of compatible sterilization cycle options; and (f) configuring the sterilization cycle based upon the selection.

3. The method of claim 1, wherein configuring the at least one risk mitigation process comprises the steps:

(i) accessing a database and retrieving a set of medical device records, (ii) determining an approved cycle configuration based upon the identity of the medical device and the set of medical device records, and (iii) configuring the sterilization cycle based upon the approved cycle configuration.

4. The method of claim 3, wherein the approved cycle configuration is associated with a device assurance indicator, wherein the device assurance indicator is configured to be received based upon the identity of the medical device, wherein the device assurance indicator is further configured to indicate that the medical device is compatible with the sterilization cycle.

5. The method of claim 1, further comprising the steps, when the device assurance indicator indicates that the medical device is compatible:

(i) indicating via a display that the sterilization cycle is compatible with the medical device, and (ii) upon completion of the sterilization cycle, adding a compatibility assured indicator to a cycle result dataset, wherein the cycle result dataset describes the performance of the sterilization cycle and the compatibility assured indicator indicates that the medical device was compatible with the sterilization cycle.

6. The method of claim 5, further comprising the steps, when the device assurance indicator indicates that the medical device is not assured as compatible:

(i) displaying via the display a compatibility warning that indicates the sterilization cycle is not assured as compatible with the medical device, (ii) receiving a confirmation via a user input to override the compatibility warning and proceed with the sterilization cycle, (iii) providing an unverified cycle alert via a communication device as an electronic message to one or more recipients, and (iv) upon completion of the sterilization cycle, adding an assurance warning indicator to a cycle result dataset, wherein the cycle result dataset describes the performance of the sterilization cycle and the compatibility assured indicator indicates that the medical device was not assured as compatible with the sterilization cycle.

7. The method of claim 1, further comprising causing a device cycle summary interface to display via a display, wherein the device cycle summary interface comprises:

(A) a sterilizing cabinet descriptor, (B) a list of cycle results for sterilization cycles performed on a sterilizing cabinet associated with the sterilizing cabinet descriptor, and (C) an assurance rate indicating the portion of the list of cycle results associated with a compatible device assurance indicator.

8. The method of claim 1, further comprising causing an instrumentation assurance summary interface to display via a display, wherein the instrumentation assurance summary interface comprises:

(A) a set of medical device descriptors for each medical device in service at a location, (B) a set of sterilizing equipment descriptors for sterilizing devices in service at the location, (C) a set of assurance descriptors indicating which of the sterilizing devices in service at the location are assured as compatible for each medical device in service at the location, and (D) an assurance rate indicating whether any of the medical devices in service at the location are not compatible with any sterilizing devices in service at the location.

9. The method of claim 8, wherein the instrumentation assurance summary interface further comprises a request assurance feature associated with an unverified medical device of the set of medical device descriptors;

wherein the request assurance feature is configured to be interacted with via a user input to cause an electronic communication to be sent to a recipient associated with a sterility guide database;

wherein the electronic communication describes the unverified medical device and the set of sterilizing equipment descriptors.

10. The method of claim 1, wherein:

(a) the device indicator includes a set of device tracking information received from the sterilization system;

(b) the set of device tracking information indicates an in-transit medical device leaving from an origin and having a destination of the device; and (c) the set of medical device records associates the in-transit medical device with the identity of the medical device; and (d) the method further comprises determining that the medical device is the in-transit medical device.

11. The method of claim 1, wherein:

(a) the method further comprises:

(i) an optical reader reading data encoded in an optical identifier; and (ii) receiving the data indicator after the optical reader reads the optical identifier; and (b) the set of medical device records associates the optical identifier with the identity of the medical device.

12. The method of claim 1, wherein:

(a) the method further comprises a text input receiving the device indicator as a text identifier; and (b) the set of medical device records associates the text identifier with the identity of the medical device.

13. A method for configuring a sterilization system to sterilize a medical device comprising the steps:

(a) receiving a device indicator that is associated with the medical device;

(b) accessing a set of medical device records;

(c) determining an identity of the medical device based upon an association of the device indicator with the set of medical device records;

(d) configuring at least one risk mitigation process based upon the identity of the medical device;

(e) configuring a sterilization cycle to be performed on the medical device based upon the at least one risk mitigation process;

(f) after the identity of the medical device is determined, displaying the identity to a user via a display;

(g) receiving an identity response from a user via a user interface;

(h) where the identity response indicates that the identity is not correct, providing a manual device input interface via the display, wherein the manual device input interface comprises a set of prompts for additional information operable by the user to determine a new identity of the medical device; and (i) configuring the at least one risk mitigation process based upon the new identity instead of the identity.

14. The method of claim 13, wherein:

(a) the device indicator includes a set of device tracking information received from the sterilization system;

(b) the set of device tracking information indicates an in-transit medical device leaving from an origin and having a destination of the device;

(c) the set of medical device records associates the in-transit medical device with the identity of the medical device; and (d) the method further comprises determining that the medical device is the in-transit medical device.

15. The method of claim 13, wherein the at least one risk mitigation process comprises an automatic cycle section, wherein the automatic cycle section comprises:

(a) determining an approved cycle configuration based upon the identity of the medical device; and (b) configuring the sterilization cycle based upon the approved cycle configuration.

16. The method of claim 15, wherein the approved cycle configuration is associated with a device assurance indicator, wherein the device assurance indicator is configured to be received from a sterility guide database based upon the identity of the medical device, wherein the device assurance indicator is further configured to indicate that the medical device is compatible with the sterilization cycle.

17. The method of claim 13, wherein configuring the at least one risk mitigation process comprises the steps:

(i) determining a sterilizing cabinet identifier associated with the sterilization cycle, (ii) determining a sterilization cycle type associated with the sterilization cycle, and (iii) receiving a device assurance indicator from a sterility guide database of the sterilization system based upon the sterilizing cabinet identifier, the sterilization cycle type, and the identity of the medical device, and wherein the device assurance indicator indicates whether the medical device is compatible with a sterilizing cabinet associated with the sterilizing cabinet identifier and a sterilization cycle associated with the sterilization cycle type.

18. A method for configuring a sterilization system to sterilize a medical device comprising the steps:

(a) receiving a device indicator that is associated with the medical device;

(b) accessing a set of medical device records;

(c) determining an identity of the medical device based upon an association of the device indicator with the set of medical device records;

(d) configuring at least one risk mitigation process based upon the identity of the medical device; and (e) configuring a sterilization cycle to be performed on the medical device based upon the at least one risk mitigation process;

wherein configuring the at least one risk mitigation process comprises the steps:

(A) determining a sterilizing cabinet identifier associated with the sterilization cycle, (B) determining a sterilization cycle type associated with the sterilization cycle, and wherein the at least one risk mitigation process comprises an automatic cycle selection, the automatic cycle selection comprising:

(i) determining an approved cycle configuration based upon the identity of the medical device; and (ii) configuring the sterilization cycle based upon the approved cycle configuration;

wherein the approved cycle configuration is associated with a device assurance indicator, wherein the device assurance indicator is configured to be received from a sterility guide database based upon the identity of the medical device, wherein the device assurance indicator is further configured to indicate that the medical device is compatible with the sterilization cycle, wherein the device assurance indicator is further configured to indicate whether the medical device is compatible with a sterilizing cabinet associated with the sterilizing cabinet identifier and a sterilization cycle associated with the sterilization cycle type.

19. The method of claim 18, wherein:

(a) the device indicator includes a set of device tracking information received from the sterilization system;

(b) the set of device tracking information indicates an in-transit medical device with the identity of the medical device;

(c) the set of medical device records associates the in-transit medical device with the identity of the medical device; and (d) the method further comprises determining that the medical device is the in-transit medical device.

* * * * *